(12) United States Patent
Pacheco

(10) Patent No.: US 10,471,263 B2
(45) Date of Patent: Nov. 12, 2019

(54) SYSTEM AND METHOD FOR CARDIAC RESYNCHRONIZATION

(71) Applicant: Catheter Precision, Inc., Ledgewood, NJ (US)

(72) Inventor: Robert Pacheco, Bayside, NY (US)

(73) Assignee: Catheter Precision, Inc., Mt. Olive, NJ (US)

( * ) Notice: Subject to any disclaimer, the term of this patent is extended or adjusted under 35 U.S.C. 154(b) by 66 days.

(21) Appl. No.: 15/695,332

(22) Filed: Sep. 5, 2017

(65) Prior Publication Data

US 2018/0064947 A1    Mar. 8, 2018

Related U.S. Application Data

(60) Provisional application No. 62/383,804, filed on Sep. 6, 2016.

(51) Int. Cl.
*A61B 5/0402* (2006.01)
*A61N 1/372* (2006.01)
(Continued)

(52) U.S. Cl.
CPC ........ *A61N 1/37247* (2013.01); *A61B 5/0033* (2013.01); *A61B 5/0044* (2013.01);
(Continued)

(58) Field of Classification Search
CPC .... A61N 1/37247; A61B 5/04; A61B 5/0402; A61B 5/4836
See application file for complete search history.

(56) References Cited

U.S. PATENT DOCUMENTS

| 7,787,951 B1 | 8/2010 | Min |
| 8,155,739 B2 | 4/2012 | Keel et al. |

(Continued)

FOREIGN PATENT DOCUMENTS

| WO | 2012061612 A2 | 5/2012 |
| WO | 2013006713 A2 | 1/2013 |
| WO | 2015170978 A1 | 11/2015 |

OTHER PUBLICATIONS

Daubert, et al., "Avoiding non-responders to cardiac resynchronization therapy: a practical guide", European Heart Journal Advance Access, European Heart Journal, doi:10.1093/eurheartj/ehw270, 13 pages, (Jul. 1, 2016).

(Continued)

*Primary Examiner* — Joseph M Dietrich
(74) *Attorney, Agent, or Firm* — The Marbury Law Group, PLLC

(57) ABSTRACT

Various embodiments include methods for conducting cardiac resynchronization therapy and systems implementing the method. Various embodiments may include generating, using a processing unit, a three-dimensional (3D) activation map showing the propagation of electrical signals through a heart of a patient, identifying a stimulation point on the heart for cardiac resynchronization; generating real-time images of the heart, displaying, on a display unit, the stimulation point on the real-time images as a virtual stimulation point, implanting a pacing device into the patient at the identified stimulation point, such that the pace maker is aligned with the virtual stimulation point in the real-time images, and stimulating the heart using the pacing device.

19 Claims, 13 Drawing Sheets

(51) Int. Cl.
*A61B 5/00* (2006.01)
*A61B 6/00* (2006.01)
*A61N 1/362* (2006.01)
*A61N 1/365* (2006.01)
*A61B 5/04* (2006.01)
*A61N 1/368* (2006.01)
*A61B 5/0452* (2006.01)
*A61B 6/03* (2006.01)
*A61B 5/042* (2006.01)
*A61B 5/11* (2006.01)

(52) U.S. Cl.
CPC .............. *A61B 5/04* (2013.01); *A61B 5/0402* (2013.01); *A61B 5/04012* (2013.01); *A61B 5/0452* (2013.01); *A61B 5/4836* (2013.01); *A61B 5/686* (2013.01); *A61B 5/6869* (2013.01); *A61B 5/72* (2013.01); *A61B 5/7203* (2013.01); *A61B 5/743* (2013.01); *A61B 6/503* (2013.01); *A61N 1/368* (2013.01); *A61N 1/3627* (2013.01); *A61N 1/36507* (2013.01); *A61N 1/37205* (2013.01); *A61B 5/0422* (2013.01); *A61B 5/1107* (2013.01); *A61B 5/7271* (2013.01); *A61B 6/032* (2013.01)

(56) References Cited

U.S. PATENT DOCUMENTS

| | | |
|---|---|---|
| 2009/0099679 A1 | 4/2009 | Sandoval et al. |
| 2010/0268059 A1 | 10/2010 | Ryu et al. |
| 2012/0157822 A1 | 6/2012 | Van Dam et al. |
| 2017/0011197 A1 | 1/2017 | Van Dam et al. |

OTHER PUBLICATIONS

Ploux, et al., "Noninvasive Electrocardiographic Mapping to Improve Patient Selection for Cardiac Resynchronization Therapy", Cardiac Resynchronization, Journal of the American College of Cardiology, vol. 61, No. 24, ISSN 00735-1097, 9 pages, (2013).
International Search Report and the Written Opinion of the International Searching Authority from the European Patent Office in Application No. PCT/US2017/050188 dated Nov. 7, 2017.
International Bureau, International Preliminary Report on Patentability dated Mar. 21, 2019 for International Application No. PCT/US2017/050188, 9 pages.

SYSTEM AND METHOD FOR CARDIAC RESYNCHRONIZATION

RELATED APPLICATIONS

This application claims the benefit of priority to U.S. Provisional Patent Application No. 62/383,804 entitled "System and Method for Cardiac Resynchronization" filed Sep. 6, 2016, the entire contents of which are hereby incorporated by reference.

BACKGROUND

Some heart defects in the conduction system result in asynchronous contraction of the heart, which are sometimes referred to as conduction disorders. As a result, the heart does not pump enough blood, which may ultimately lead to heart failure. Conduction disorders can have a variety of causes, including age, heart (muscle) damage, medications and genetics.

A common cause for conduction disorders results from defects in the left and/or right ventricle fast activation fibers, the His-Purkinje system, or scar tissue. As a result, the left and right ventricles may not be synchronized. This is referred to as Left Bundle Branch Block (LBBB) or Right Bundle Branch Block (RBBB). A known way to improve heart function in case of LBBB or RBBB is cardiac resynchronization therapy (CRT), which is also known as biventricular pacing or multisite ventricular pacing. CRT involves simultaneous pacing of the right ventricle (RV) and the left ventricle (LV) using a pacemaker. To implement CRT, a coronary sinus (CS) lead is placed for LV pacing in addition to a conventional RV endocardial lead (with or without a right atrial (RA) lead). The basic goal of CRT is to improve the mechanical functioning of the LV by restoring LV synchrony in patients with dilated cardiomyopathy and a widened QRS period, which is predominantly a result of LBBB.

Currently, the proper positioning of leads to obtain maximum cardiac synchronization involves a certain amount of guesswork on the part of an operating physician. In particular, current methods do not allow for the determination of the optimal location for pacemaker leads, on a patient by patient basis. Further, current methods do not allow for the real time determination of whether leads have been properly positioned.

The lack of such a method may contribute to the 30% of patients that fail to respond to CRT. Accordingly, there is a need for improved CRT methods.

SUMMARY

Various embodiments provide methods for performing cardiac resynchronization therapy and a system implementing the methods. Various embodiments may include generating, using a processing unit, a three-dimensional (3D) activation map showing the propagation of electrical signals through a heart of a patient; identifying a stimulation point on the heart for cardiac resynchronization; generating real-time images of the heart; displaying, on a display unit, the stimulation point on the real-time images as a virtual stimulation point; implanting a pacing device into the patient at the identified stimulation point, such that the pace maker may be aligned with the virtual stimulation point in the real-time images; and stimulating the heart using the pacing device.

Various embodiments provide a cardiac resynchronization system including a processing unit having an activation map generator configured to generate a 3D activation map of the heart of a patient; a synchronicity determination unit configured to calculate ventricle synchronicity of the heart, based on the activation map; a stimulation point generator configured to an identify stimulation point on the heart for increasing the synchronicity of the heart. The cardiac resynchronization system may further include a display configured to display real-time images of the heart; and an image integrator configured to add virtual stimulation points to the real-time images, the virtual stimulation points corresponding to the identified stimulation points.

Various embodiments may include a cardiac resynchronization method, including: generating, using a processing unit, a three-dimensional (3D) activation map showing the propagation of electrical signals through a heart of a patient while the heart is stimulated using a pacing device implanted in the patient; adjusting stimulation parameters of the pacing device based on the activation map; and updating the activation map based on the adjusted stimulation parameters.

BRIEF DESCRIPTION OF THE DRAWINGS

The accompanying drawings, which are incorporated herein and constitute part of this specification, illustrate example embodiments of the invention, and together with the general description given above and the detailed description given below, serve to explain the features of the invention.

DETAILED DESCRIPTION

Figure 1:
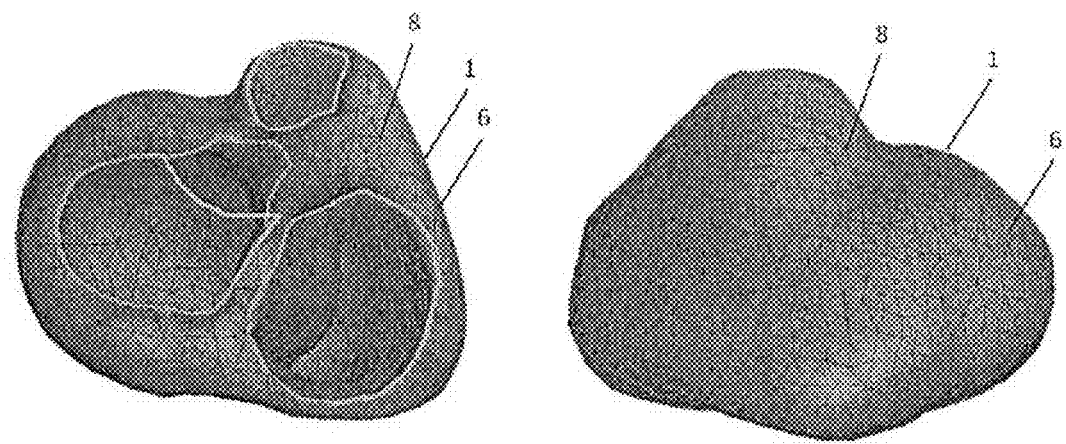
FIG. 1 is an example of a three-dimensional model of a heart.

The various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the invention or the claims.

An ECG is defined herein as any method that (preferably non-invasively) correlates actual electrical activity of the heart muscle to measured or derived (electrical activity) of the heart. In case of a classical electrocardiogram the differences in potential between electrodes on the body surface are correlated to the electrical activity of the heart. Derived ECG's can also be obtained in other ways (e.g. by measurement made by a so-called ICD (Implantable Cardioverter Defibrillator)). In order to obtain such a functional image an estimation of the movement of the electrical activity has to be provided.

Cardiac dyssynchrony has deleterious effects on cardiac function by depressing left ventricular (LV) mechanical performance, while increasing myocardial oxygen consumption. In addition, it probably causes LV remodeling. Therefore, cardiac dyssynchrony accelerates the progression of chronic congestive heart failure (CHF) and reduces patient survival.

During normal conduction, cardiac activation begins within both the left ventricular (LV) and right ventricular (RV) endocardium. In particular, electrical impulses (i.e., depolarization waves) travel substantially simultaneously through both the left and right ventricles. Bundle branch block (BBB) is a condition in which there's a delay or obstruction along the pathway that the electrical impulses. The delay or blockage may occur on the pathway that sends electrical impulses to the left or the right ventricles.

Left BBB is a condition in which the electrical impulses to the LV are slowed, and is one of the leading causes of cardiac desynchronization. In particular, activation begins only in the RV and proceeds through the septum before reaching the LV endocardium.

A pacemaker is an electronic device, approximately the size of a pocket watch, which senses intrinsic heart rhythms and provides electrical stimulation when indicated. Cardiac pacing can be either temporary or permanent.

Permanent pacing is most commonly accomplished through transvenous placement of leads to the endocardium (i.e., right atrium or ventricle) or epicardium (i.e., the LV surface via the coronary sinus), which are subsequently connected to a pacing generator placed subcutaneously in the infra-clavicular region. However, miniaturized pacemakers (i.e., micro-pacemakers) have been developed for implantation directly on or in the heart. Accordingly, the present disclosure encompasses endocardial and epicardial pacing, which may be accomplished using pacing electrodes connected to a pacing generator and/or implantable micro-pacemakers.

Cardiac resynchronization therapy (CRT) is a specialized type of pacemaker therapy that provides biventricular pacing. CRT is carried out with or without the use of an implantable cardioverter-defibrillator (ICD), a device employed for treatment and prophylaxis in patients at risk for ventricular tachycardia (VT) or ventricular fibrillation (VF).

FIG. 1 shows a three dimensional (3D) model of a heart 1 seen in two different directions. The 3D model includes a mesh 6 representing an outer surface of the heart, here the myocardial surface. In this example the 30 model also may include the septal wall. The mesh 6 has a plurality of nodes 8. In this example, the mesh is a triangular mesh in which the surface of the heart is approximated by adjoining triangles.

Figure 2A:
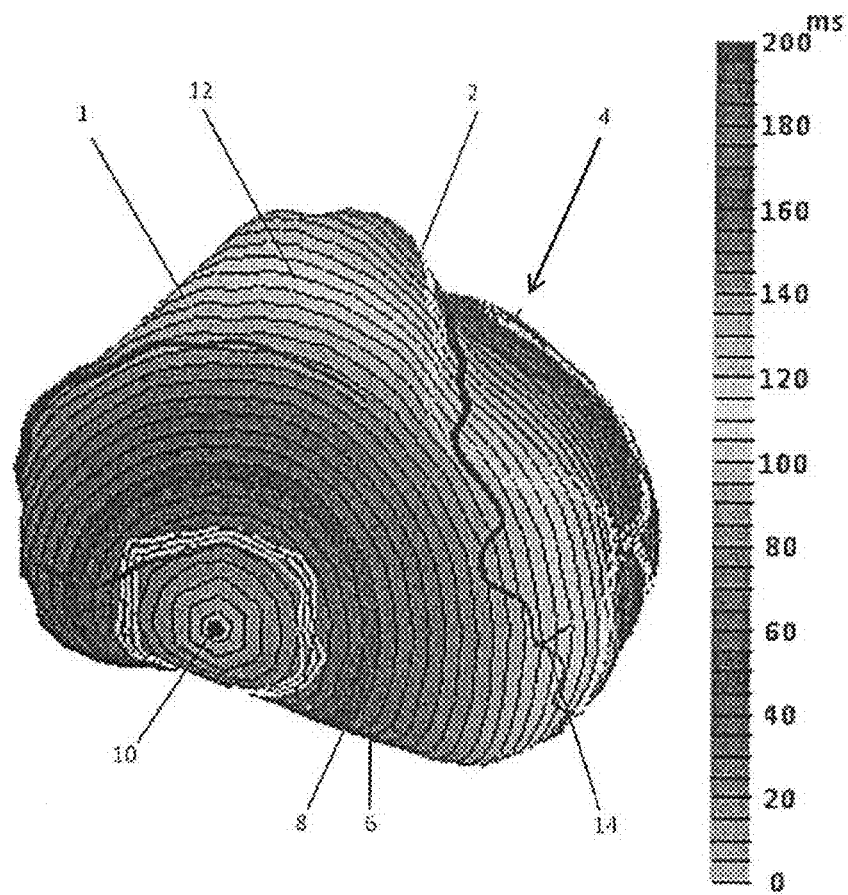
FIG. 2A is a plan view of a 3D model of electrical activation of a heart.

FIG. 2A is a 3D model 4 showing the initial electrical activation of a heart 1 from a single stimulation location 10. In particular, FIG. 2A shows a ventricular surface of the myocardium with a septal wall 2. In general, the 3D model 4 may include a mesh 6 representing a ventricular surface of the heart, here an outer surface of the ventricular myocardium with septal wall as represented in FIG. 1. The mesh 6 has a plurality of nodes 8. In the illustrated example, the heart 1 is electrically stimulated at a stimulation location 10. Upon electrical stimulation at the stimulation location 10, the electrical signals will travel through the heart tissue. Hence, different parts of the heart will be activated at different times. Each location on the heart has a particular delay relative to the initial stimulation. Each node 8 has associated therewith a value representative of a time delay between stimulation of the heart 1 at the stimulation location 10 and activation of the heart at that respective node 8. Locations that share the same delay time are connected by isochrones 12 in FIG. 2A. Herein, isochrones are defined as lines drawn on a 3D heart surface model connecting points on this model at which the activation occurs or arrives at the same time. The delay time for nodes across the heart surface in this example is also displayed by differing rendering colors. The vertical bar indicates the time delay in milliseconds associated with the respective colors. The stimulation location 10 can be the location of intrinsic activation of the heart 1.

Figure 3:
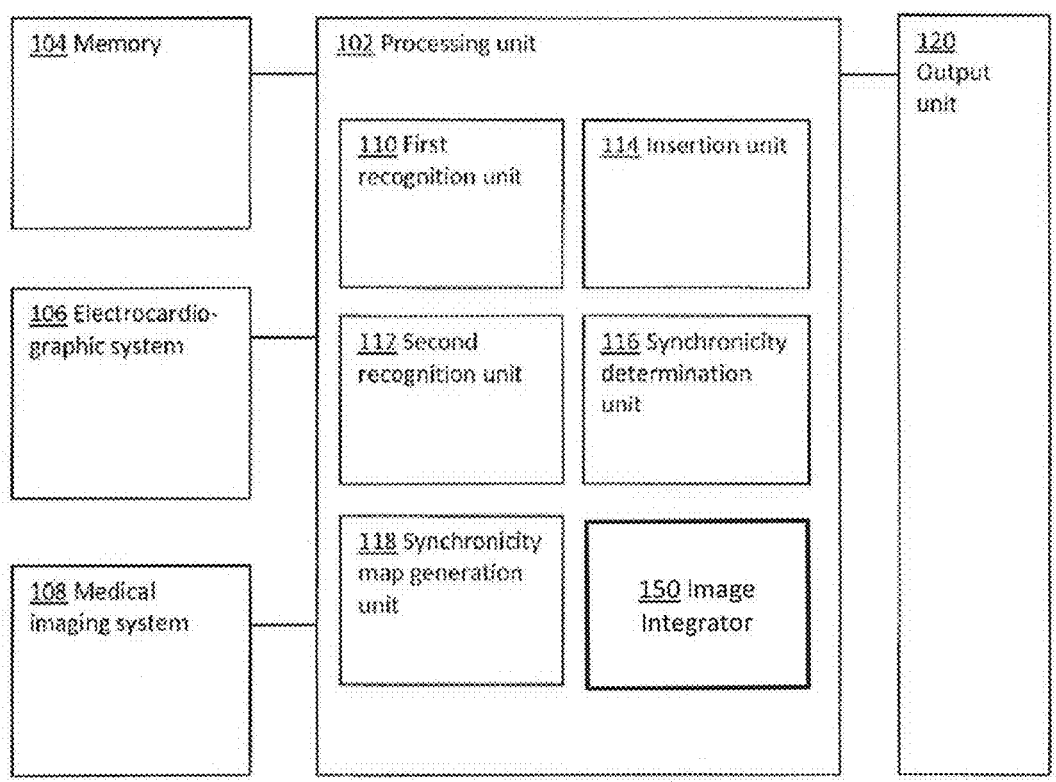
FIG. 3 is a schematic representation of a cardiac imaging system according to various embodiments of the present disclosure.

FIG. 3 is a schematic representation of a system 100 for providing a representation of synchronicity of electrical activation of heart tissue. The system 100 includes a processing unit 102 and a memory 104.

The 3D electrical activation model 4 can be obtained by combining electrocardiographic and medical imaging data. This data may be stored in the memory 104. The processing unit 102 may be connected to an electrocardiographic system 106 and a medical imaging system 108 for retrieving the data and storing corresponding data in the memory 104. An electrocardiographic imaging (ECGI) method able to determine the cardiac activation from a 12 lead ECG may be applied by the processing unit 102 for determining the 3D model 4 of electrical activation of the heart. The ECG signals may be combined with a patient-specific three-dimensional anatomical model of the heart, lungs, and/or torso, in order to compute the positions of the cardiac isochrones. The patient-specific 3D anatomical model may be obtained from a magnetic resonance image (MRI) or computed tomography (CT) images. Alternatively or additionally, a 3D anatomical model showing closest conformity to the patient may be selected, and optionally modified, from a database including a plurality of 3D anatomical models. The selected, and optionally modified, 3D anatomical model may serve as the patient-specific 3D anatomical model.

The 3D electrical activation model 4 may also include further information. In the example of FIG. 2A, the 3D model 4 may include cardiac blood vessels 14 and/or veins on the myocardium. This information may be added to the 3D model 4 in that nodes are indicated as being associated with such blood vessel. The blood vessels 14 may then be identified and optionally shown in the 3D model 4. Optionally, the processing unit 102 may include a first recognition unit 110 arranged for automatically retrieving information representative of the location of such blood vessels from the patient's 3D anatomical model of the heart. The processing unit 102 may then automatically insert this information into the 3D model 4.

The 3D model 4 may also include information on scar tissue. Scar tissue locations may be obtained from delayed enhancement MRI images and added to the 3D model 4. Scar tissue can be simulated in the 3D model 4 by reducing the propagation velocity of electrical signals there through. Scar tissue can also be accounted for by selling the transition from one node to another to very slow or non-transitional for the areas in the heart wall where scar tissue is present. Optionally, the processing unit 102 may include a second recognition unit 112 arranged for automatically retrieving information representative of the location of such scar tissue from the patient-specific three-dimensional anatomical model of the heart. The processing unit 102 may then automatically insert this information into the 3D model 4.

In various embodiments, the obtained 3D model 4 may be used for obtaining further information on electrical activation of the heart. For example, the time delay of activation from one node to another may be determined. This may be used to generate, on the basis of the 3D model 4, other views resulting from initial stimulation at other nodes of the mesh 6. Thereto, the processing unit 102 may include an insertion unit 114. The insertion unit 114 may take the 3D model 4 and define a certain node as a stimulation location. The 3D model 4 may assume stimulation at a predetermined node. The insertion unit 114 may remove stimulation at that predetermined node for calculation purposes.

Figure 2B:
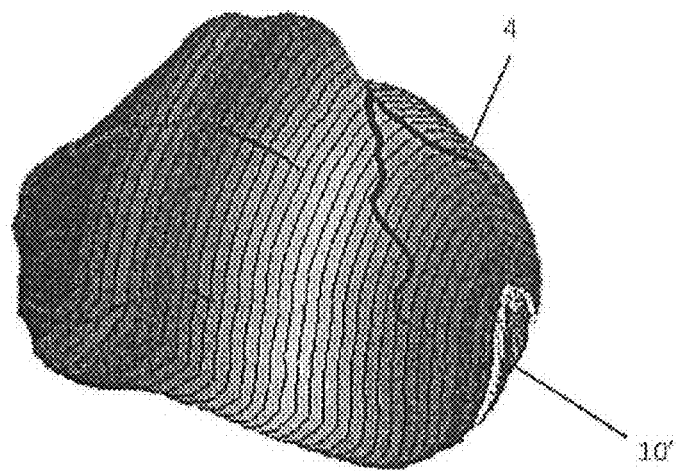
FIG. 2B is a plan view of a 3D model of electrical activation of a heart.

FIG. 2B shows an example resulting from initial stimulation at another stimulation location 10'. A view resulting from initial stimulation at other nodes of the mesh 6 may be generated for each node of the mesh 6.

A particular electrical activation sequence of the entire heart 1, resulting from stimulation at a particular node, may be summarized in a single parameter, namely, heart activation synchronicity. The heart activation synchronicity provides an indication of how synchronously the entire heart is activated. For common situations, a more synchronous activation of the heart is considered beneficial. The measure for heart activation synchronicity in this example is standard deviation (std) of the depolarization (dep) times of the heart. Hence, the heart activation synchronicity provides an indication of synchronicity of activation of the entire heart as a result of stimulation at the respective node. The processing unit 102 may include a synchronicity determination unit 116 configured to determine the heart activation synchronicity.

In various embodiments, the heart activation synchronicity may be determined separately for stimulation at each node. Hence, a measure of heart activation synchronicity for each node of the mesh may be provided. The processing unit 102 may include a synchronicity map generation unit 118 configured to generate a synchronicity map based on the calculation of the heart activation synchronicity for each node, by the synchronicity determination unit 116. The processing unit 102 may be connected with an output unit 120 arranged for outputting the synchronicity map 15 and/or alternative data to a user. The output unit may be a display unit, a printer, a messaging unit, or the like.

Figure 2C:
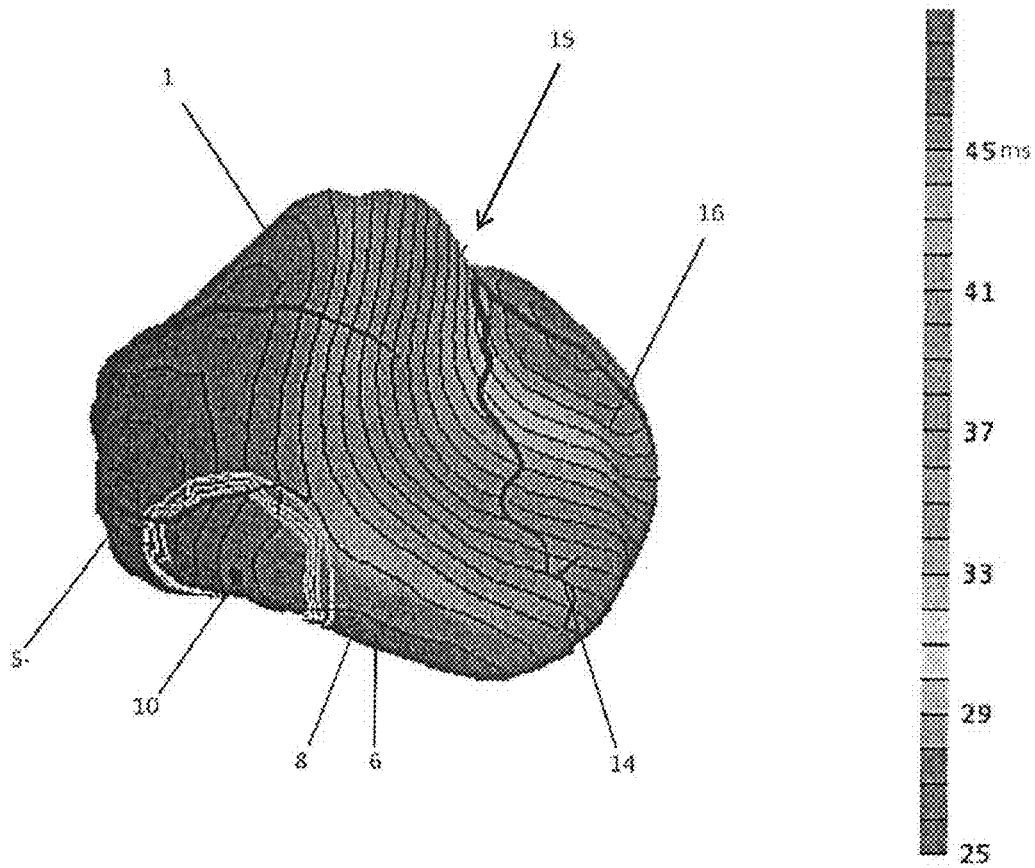
FIG. 2C is a plan view of a synchronicity map according to various embodiments of the present disclosure.
Figure 2D:
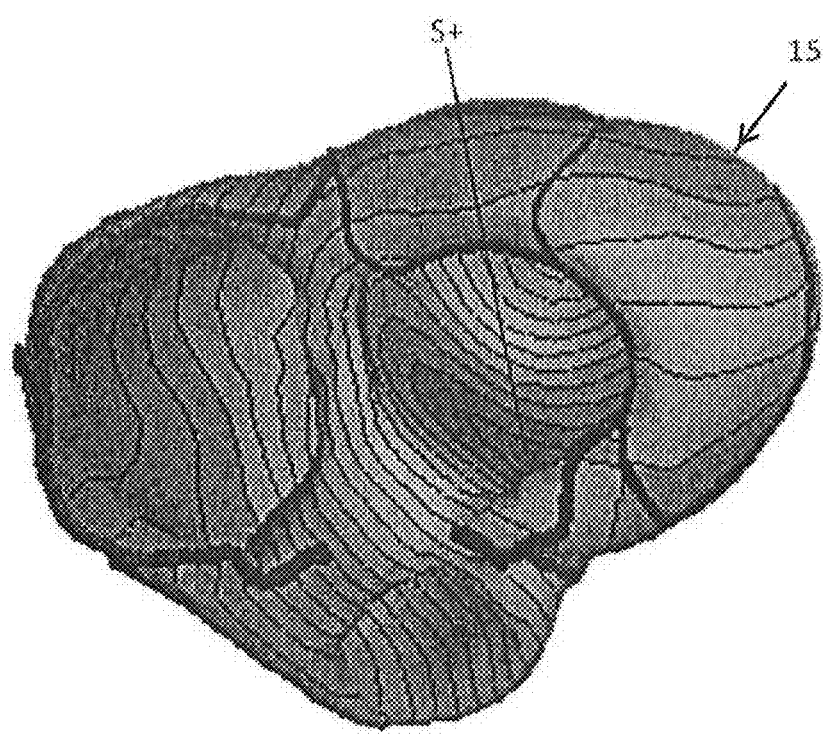
FIG. 2D is a plan view of a synchronicity map according to various embodiments of the present disclosure.

FIG. 2C shows an example of a heart synchronicity map 15. In FIG. 2C, heart activation synchronicity is indicated for each node in the map 15. In this example, the indication may be show by providing false colors and/or iso-sync lines 16. The iso-sync lines 16 connect nodes having the same heart activation synchronicity. The heart synchronicity map 15 provides a singular 3D overview showing which locations on the heart result in good heart activation synchronicity, and which locations on the heart result in poor heart activation synchronicity, if the heart were stimulated at such locations. In this example, it can be seen that the original stimulation location 10 does not provide particularly good synchronization, with a heart activation synchronicity value of approximately 45 ms standard deviation of the depolarization times of the heart. The least favorable stimulation location, here the location with the highest heart activation synchronicity value, is indicated at S−. In this example, the most favorable stimulation location, where the lowest heart activation synchronicity value occurs, is indicated at S+. It is noted that the most favorable stimulation location S+ may best be seen when looking at the synchronicity map 15 from another direction, as shown in FIG. 2D.

Another example of a measure for heart activation synchronicity is a range in depolarization times (maximum depolarization time−minimum depolarization time). The range in depolarization times may be corrected for cycle length. Another example of a measure for heart activation synchronicity is a standard deviation of the Left Ventricle (LV) depolarization times only. Another example of a measure for heart activation synchronicity is a delay between stimulus and Septum activation. Another example of a measure for heart activation synchronicity is an AV delay. Another example of a measure for heart activation synchronicity is a VV delay. The measure for heart activation synchronicity may be chosen in dependence of the task at hand and/or in dependence of a specific condition or abnormality experienced in the patient.

Figure 4A:
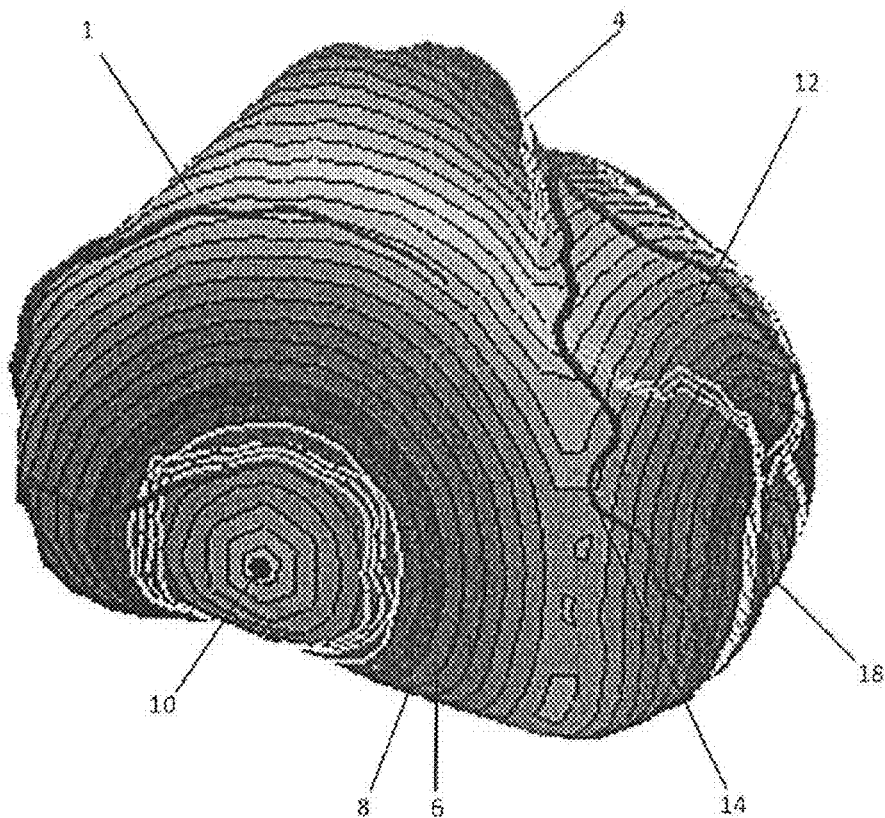
FIGS. 4A and 4B are plan views of 3D models of the electrical activation of a heart according to various embodiments of the present disclosure.

In FIG. 4A, a second example is shown in which a second stimulation location 18 is defined. Then electrical activation of the heart is calculated using the 3D model 4 and simultaneous stimulation at the first stimulation location 10 and the second stimulation location 18. In this example, the insertion unit 114 does not remove stimulation at the first location 8 for calculation purposes. FIG. 4A shows the calculated resulting electrical activation of the heart 1. The total activation time shortens due to the addition of the second stimulation location 18. In this example, the first stimulation location 10 represents the location of intrinsic activation of the heart, or a first chosen location to stimulate or a stimulation generated by an already present pacemaker lead within the heart.

Figure 4B:
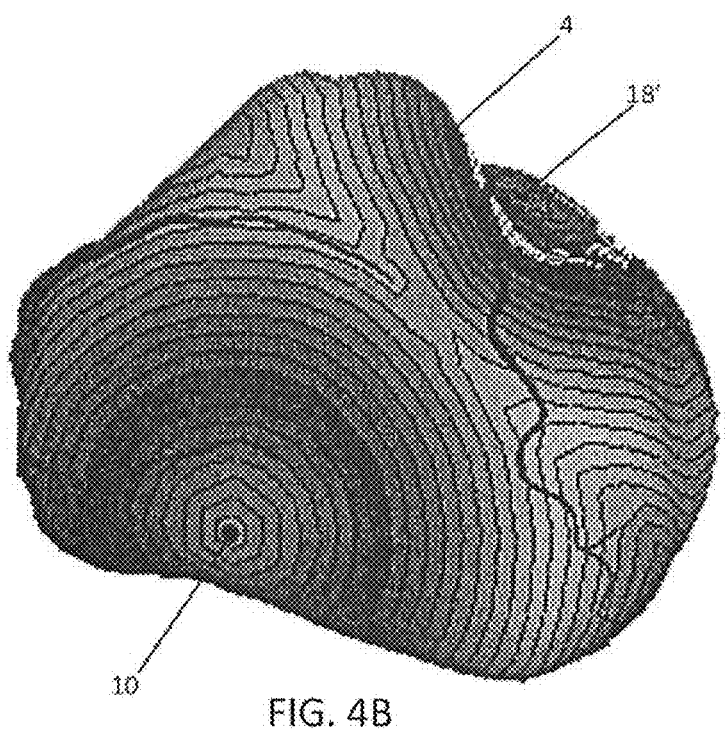

FIG. 4B shows an example resulting from initial stimulation at a second stimulation location 18' simultaneous with stimulation at first stimulation location 10. A view resulting from initial stimulation at second nodes of the mesh 6 simultaneous with stimulation at a first node associated with the first stimulation location 10 may be generated for each node of the mesh 6.

Figure 4C:
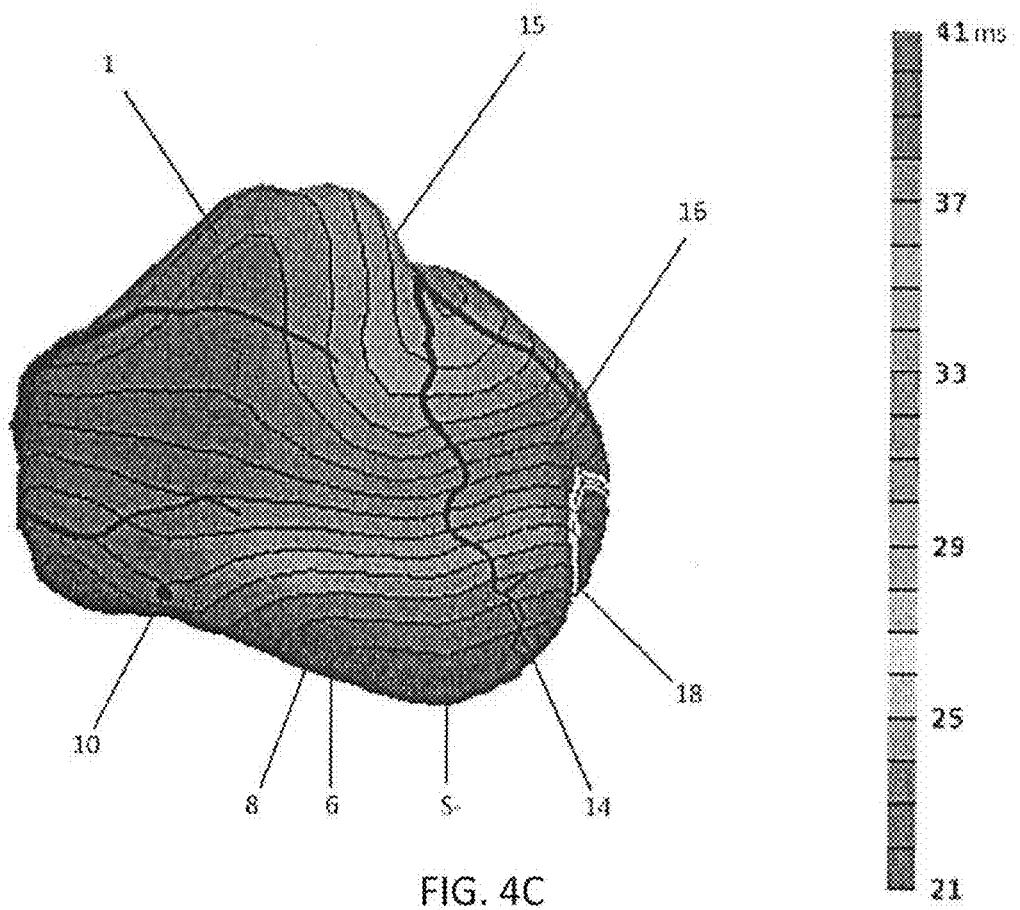
FIGS. 4C and 4D are plan views of synchronicity maps according to various embodiments of the present disclosure.
Figure 4D:
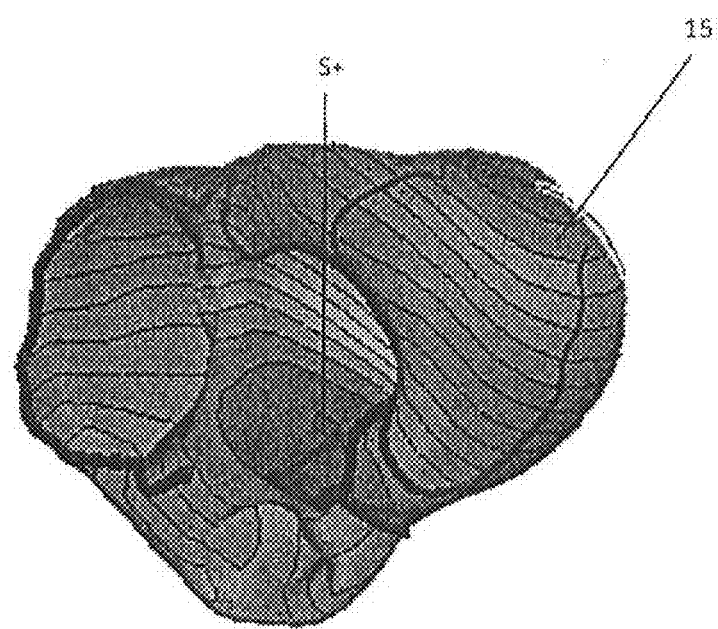

In the example of FIGS. 4C and 4D, a particular electrical activation sequence of the entire heart is combined and shown as the heart activation synchronicity. In this example, the electrical activation sequence involves stimulation at the second stimulation location 18 simultaneous with stimulation at the first stimulation location 10. The heart activation synchronicity again provides an indication of how synchronous the entire heart is activated. In some embodiments, the heart activation synchronicity may be determined separately for stimulation at each node simultaneously with stimulation at the first 10 and second 18 stimulation locations. This provides a measure of heart activation synchronicity for each node acting as third stimulation location of the mesh 6.

FIG. 4C shows an example of a heart synchronicity map showing which locations on the heart result in good heart activation synchronicity and which location on the heart result in poor heart activation synchronicity. If the heart were stimulated at such locations simultaneous with stimulation at the first stimulation location 10 and the second stimulation location 18. In this example, the least favorable third stimulation location S− had the highest heart activation synchronicity value of approximately 41 ms, when the first stimulation location 10 and the second stimulation location 18 were stimulated simultaneously. In this example, the most favorable third stimulation location S+ had the lowest heart activation synchronicity value, when with the first stimulation location 10 and the second stimulation location 18 were stimulated simultaneously. It is noted that the most favorable stimulation location S+ may best be seen when looking at the synchronicity map 15 from another direction, as shown in FIG. 4D.

Figure 5:
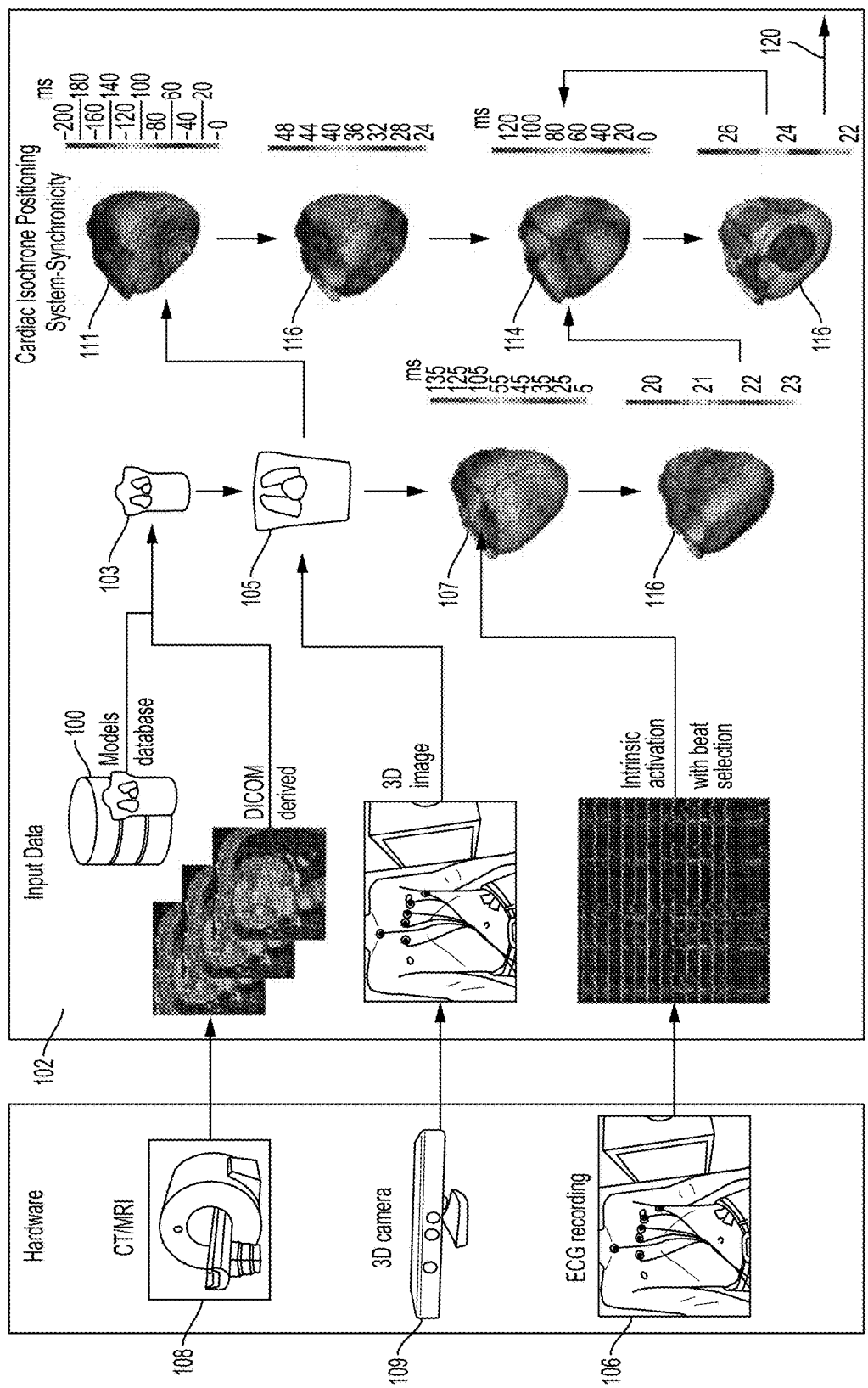
FIG. 5 is a schematic representation of a cardiac imaging system according to various embodiments of the present disclosure.
Figure 6:
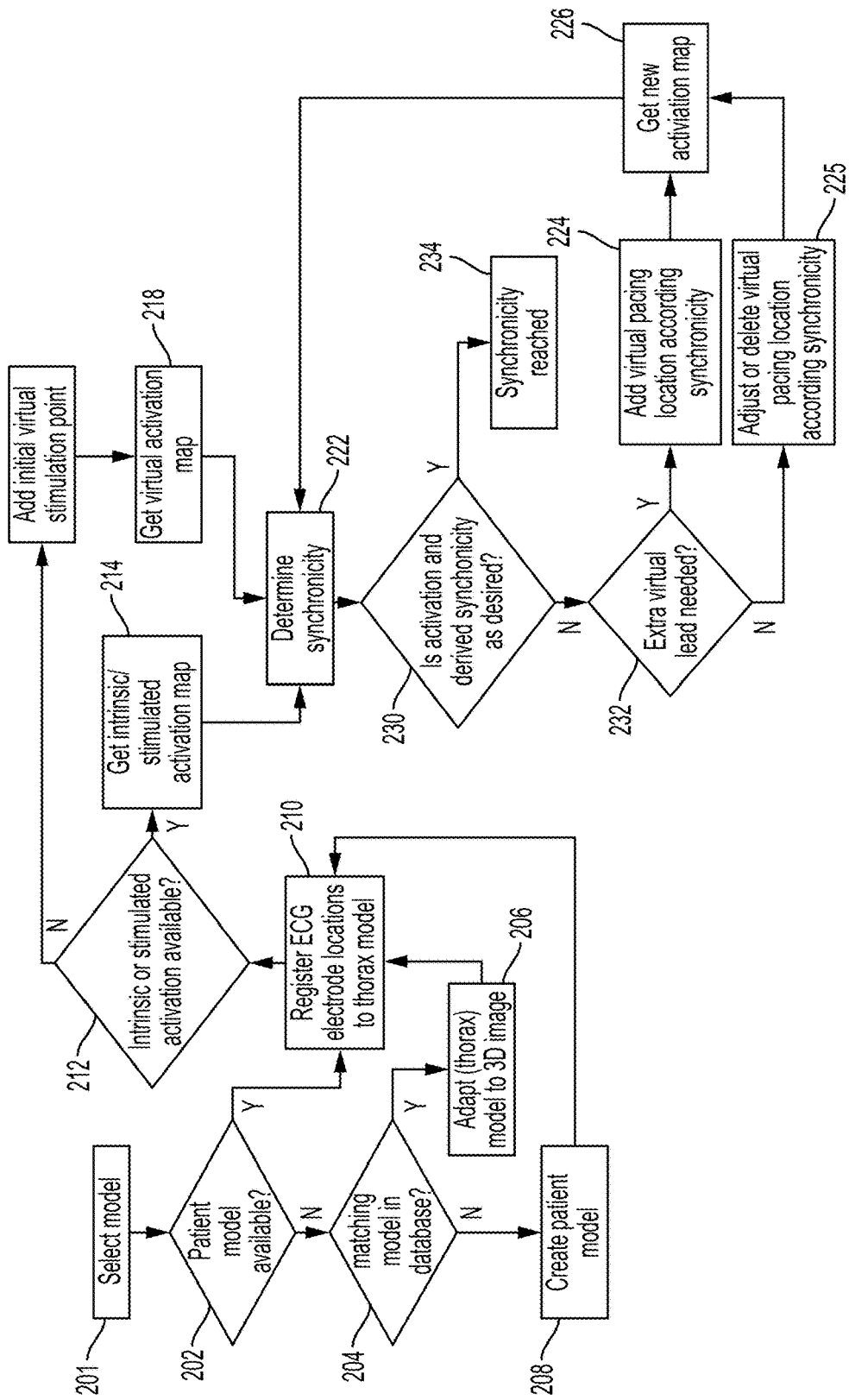
FIG. 6 is a flow chart illustrating a method according to various embodiments of the present disclosure.

FIG. 5 shows another schematic representation of a system 100 for providing a synchronicity map. FIG. 6 illustrates a method of determining heart synchronicity using the system 100 according to an embodiment. Referring to FIG. 5, the system includes a processing unit 102 which receives data from hardware modules. Optionally the processing unit 102 may receive ECG data from an electrocardiographic system 106. The processing unit may receive patient-specific anatomical data from a medical imaging system 108. Optionally, the processing unit 102 may receive information on the positions of ECG leads relative to the anatomy of the patient from a positioning system 109, such as a 3D image and the torso model mapped to the 3D image. ECG lead positions may also be entered into the system manually.

From the patient-specific anatomical data, the processing unit 102 may determine the synchronicity map 15. The processing unit 102 may include the following units, and may perform the operations illustrated in FIG. 6 and described below to generate a synchronicity map. In particular, the processing unit 102 may use a patient-specific 3D anatomical model of the thorax of the patient and the size, orientation, and location of the size, orientation, and location of the heart within the thorax. Such a model may be selected in step 201 for further use by the processing unit. Such model may already be available in step 202. If the model is not yet available, a retrieval unit 103 may check whether a suitable anatomical model for this patient is present in a database 117 in step 204. If so, the retrieval unit 103 may retrieve the suitable anatomical model from the database 117.

In step 206, the retrieval unit 103 may adapt the anatomical model from the database to the 3D image of the patient so as to transform the selected anatomical model into a (quasi) patient-specific 3D anatomical model. If no suitable patient-specific anatomical model is available in the database 117, the retrieval unit 103 may generate the patient-specific anatomical model on the basis of the received patient-specific anatomical 3D image data in step 208.

Optionally, the patient-specific 3D model also may include the size, orientation and/or location of other structures in the patient, such as the lungs and/or other organs. The patient-specific 3D model may be a volume conductor model.

Using the positions of ECG leads and the patient-specific model, a lead locator module 105 may determine corresponding positions of the ECG leads in the patient-specific 3D model, to provide an enhanced patient-specific model in step 210.

In step 212, when the patient-specific anatomical model and/or the enhanced patient-specific model available, a determination is made as to whether ECG data representative of intrinsic or stimulated activation is available. In step 214, if intrinsic activation data or pacing stimulation from one or more already present pacemaker leads is available, an activation unit 107 may generate a 3D electric model of showing the current activation of the heart of the patient, on the basis of the patient-specific model and the ECG data.

If no ECG data on intrinsic or stimulated activation is available, a virtual stimulation unit 111 may add an initial virtual stimulation to an electrical model of the heart based on previously determined and/or assumed transition velocities between nodes in step 216. An assumed transition velocity may be 0.8 ms, for example. The electrical model may include arteries, veins, and/or scar tissue as explained above. In step 218, a 3D electric model of virtual activation of the heart of the patient may be generated.

From the 3D electric model of intrinsic, stimulated, or virtual activation of the heart of the patient, a synchronicity determination unit 116 may generate a synchronicity map 15 in step 222 as described above. On the basis of the synchronicity map, the processing unit 102 may determine whether the artificial stimulation location or virtual stimulation location resulted in optimal activation and synchronicity in step 230. If so, the processing unit may calculate optimal stimulation locations for a patient's heart in step 234.

If it is determined in step 230 that optimum synchronicity has not been reached, the method proceeds to step 232 in which it is determined whether an extra virtual stimulation location should be added, or if a virtual stimulation location should be moved or changed with respect to the timing parameters. This determination may be made by a clinician, by the processing unit, or by the clinician based on information or recommendations presented on a display by the processing unit. If it is determined that a virtual stimulation location should be moved or changed, the artificial or virtual stimulation location may be adjusted accordingly in step 225. In step 226, activation may be determined again. Synchronicity may then be recalculated in step 222. The process may be repeated until a desired activation is determined to be achieved in step 230.

The system may also virtually adapt the current artificial stimulation locations (i.e., pacemaker lead locations) with respect to its current stimulation parameters to reach optimum synchronicity.

The system may also be used for assessing multiple stimulations. The multiple stimulations may be a combination of intrinsic activation and stimulated activation (pacing). The multiple stimulations may be multiple stimulated pacing, for example. The user, the processing unit 102, or the clinician based on information or recommendations presented on a display by the processing unit may determine in step 232 whether an additional stimulation location (e.g., an additional pacemaker lead) would be desirable.

If an additional stimulation location is desired, an additional stimulation location may be inserted by the insertion unit 114. Then activation for the situation with the original stimulation location and the added virtual stimulation location may be determined again in step 226, and synchronicity may be recalculated in step 222. On the basis of the synchronicity map, the processing unit 102 may determine in step 230 whether the additional virtual stimulation location resulted in optimum synchronicity. If the optimum synchronicity has not been reached, the method proceeds to step 232, in which it is determined whether an extra virtual stimulation location should be added, or if a virtual stimulation location should be moved or removed, with respect to the timing parameters. In such a case, the process may be repeated one or more times.

Based on the patient specific cardiac activation model, a cardiac synchronicity model may be generated. The synchronicity model may be a 3D heart surface model including iso-sync lines. In the synchronicity model, the iso-sync lines represent the activation synchronicity of the heart. This synchronicity may be based on specific activation conditions, such as right ventricle activation at a lead position of a pacemaker.

As an example, the synchronicity model may be generated as follows. The activation isochrones for the intrinsic LBBB pattern may be determined in the following steps.

1A) A patient-specific anatomical 3D model of the heart, lungs, and thorax may be generated, e.g. on the basis of an MRI or CT image of the patient, or derived from a model taken from a database adapted to the patients dimensions, e.g. with use of the 3D camera. The anatomical 3D model may e.g. include a 3D surface model of the heart, a 3D surface model of the lungs and a 3D surface model of the thorax. A 3D surface model may be a close approximation of the actual surface, by means of a mesh of a plurality of polygons, such as triangles, connected at their corners. The interconnected corners form nodes of the mesh.

1B) An ECG, e.g. a 12-lead ECG, may be measured. The exact locations of the electrodes of the ECG device on the thorax may be recorded. The positions of the electrodes in the 3D anatomical model are used for estimating the distribution, fluctuation, and/or movement of electrical activity through heart tissue. The exact locations of the recording leads or the ECG device may be entered in the anatomical 3D representation of the thorax.

1C) Optionally, scar tissue may b e incorporated in the anatomical 3D representation of the heart. The presence and location of scar tissue may be derived from delayed enhancement MRL images.

1D) The measurements per recording lead of the ECG device may be related to the heart and torso geometry. Using an inverse procedure, the intrinsic activation may be determined. The distribution, fluctuation, and/or movement of electrical activity through heart tissue may be based upon a myocardial distance function, a fastest route algorithm, shortest path algorithm, and/or fast marching algorithm.

2) Once the activation isochrones for the intrinsic LBBB pattern have been determined, a stimulus site may be added to the intrinsic activation for each node on the heart and the desired synchronicity of the heart may be computed from the outcome. A "node" refers to an intersection point of the triangles of upon which the anatomical 3D heart model is based.

The above methods may also be used to determine an optimal location for placement of a cardiac pacemaker electrode. To determine the optimal pacing site, synchronicity maps may be computed. The intrinsic activation map, in combination with a determined stimulation point may be applied to a new cardiac isochrone positing map.

Figure 7A:
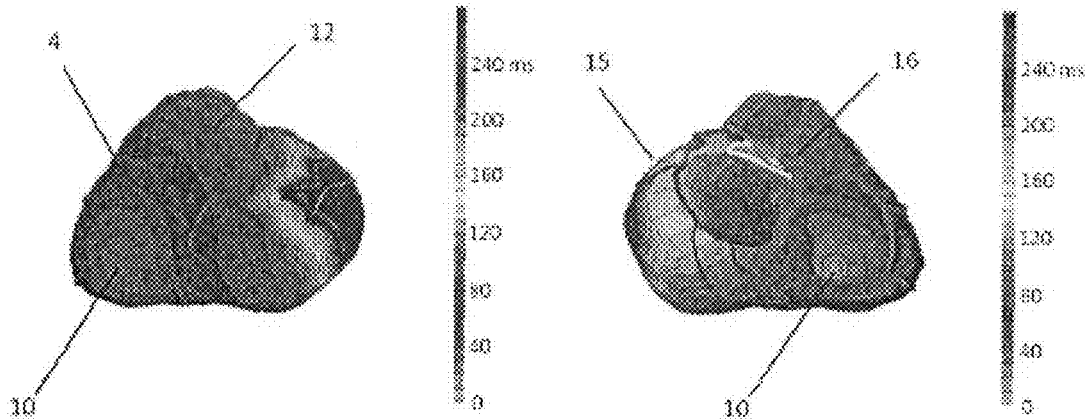
FIG. 7A is schematic representations of LAO and PA views of a 3D model of electrical activation of a heart according to various embodiments of the present disclosure.
Figure 7B:
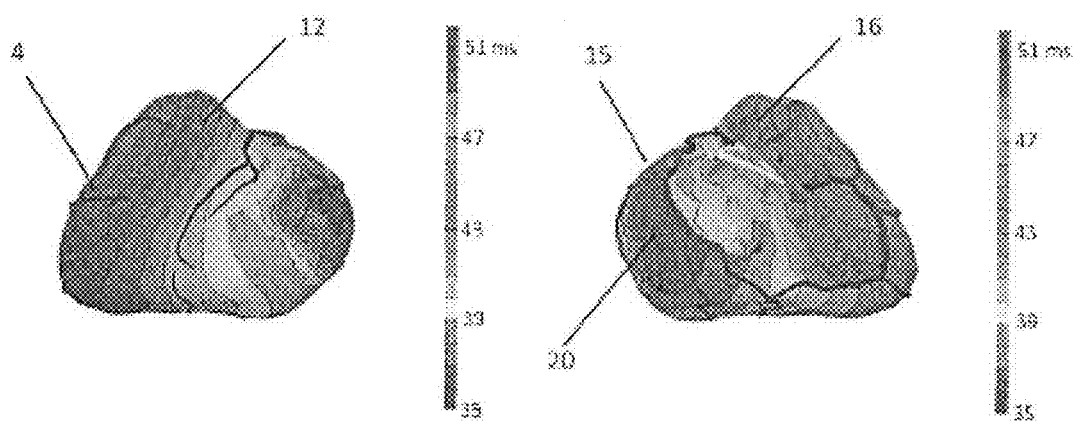
FIG. 7B is schematic representations of LAO and PA views of a synchronicity map according to various embodiments of the present disclosure.

FIG. 7A shows examples of 3D synchronization maps of LBBB activation patterns of a heart. On the left, FIG. 7A shows the left anterior oblique (LOA) view. On the right, FIG. 7A shows a postero-anterior (PA) view. FIG. 7B shows a synchronization map for the heart of FIG. 7A. On the left, FIG. 7B shows the LAO view and on the right, FIG. 7B shows the PA view.

The synchronicity map of FIG. 7B shows the standard deviation of the depolarization times of the heart as a result of one extra stimulation location combined with the intrinsic activation of the heart. From FIG. 7B it can be seen that choosing an additional stimulation location on the basal left free wall 20 reduces the standard deviation of the depolarization times of the heart the most. Therefore, in this example the area on the basal left free wall could be selected as best location for a pacemaker electrode. An updated three-dimensional model of electrical activation of the heart may be generated including intrinsic activation simultaneously with stimulation in the area on the basal left free wall.

This map may then be used to generate a new synchronicity map to check the lead location(s) in the RV. By doing this, a clinician may determine whether lead(s) should also stimulate as instead of only sensing. A clinician may also determine whether lead(s) should be shifted. A clinician may also determine whether extra stimulation lead(s) should be added. A clinician may also determine whether intrinsic AV conduction is beneficial. Intrinsic AV conduction will generally conduct to the right bundle, after which the LV needs to be activated by stimulating the LV. This may also be reversed, i.e., with a RBBB waiting for LV activation and stimulating the RV free wall at an optimal position. By repeating the procedure for both left and right ventricles, the exact location and timing of cardiac pacing can be fine-tuned.

When the intrinsic activation signal is not usable due to severe damage of the heart, the whole procedure may be performed using only simulated (pacemaker) stimulation, instead of the intrinsic activation. Steps 1B and 1D may be omitted in that case. The whole procedure will then be based on artificial activation.

Figure 8A:
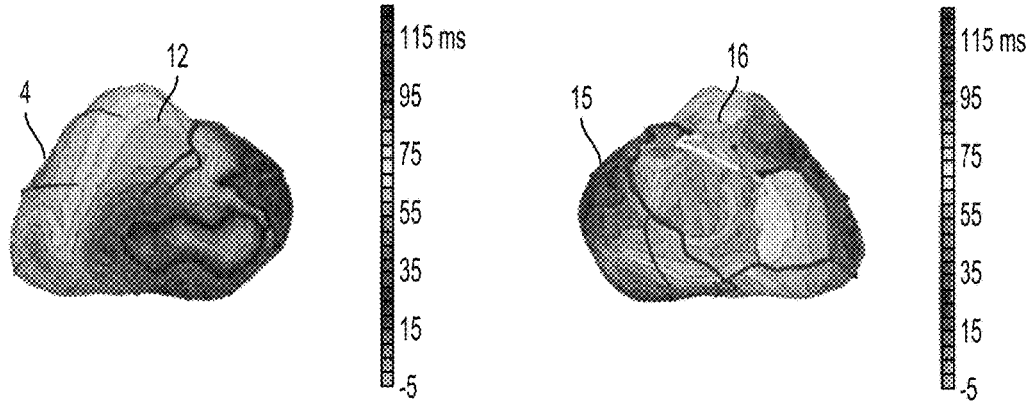
FIG. 8A is schematic representations of LAO and PA views of a 3D model of electrical activation of a heart according to various embodiments of the present disclosure.
Figure 8B:
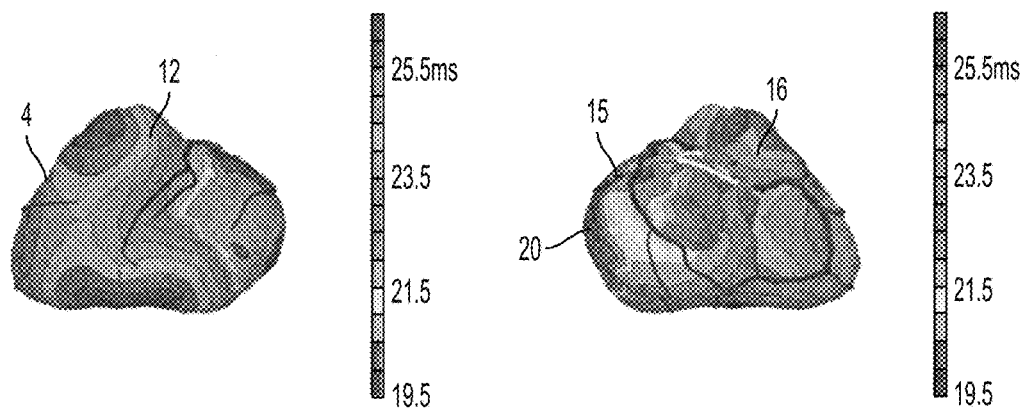
FIG. 8B is schematic representations of LAO and PA views of a synchronicity map according to various embodiments of the present disclosure.

FIG. 8A shows an example of left stimulated activation of an LBBB pattern. FIG. 8A shows the LAO view on the left, and shows the PA view on the right. FIG. 8B shows an example of a synchronicity map 15 for the heart shown in FIG. 8A. FIG. 8B shows the LAO view on the left, and shows the PA view on the right. The synchronicity map of FIG. 8B shows the standard deviation of the depolarization times of the heart as a result of one extra stimulation location combined with the left stimulated activation of the heart. From FIG. 8B it can be seen that choosing the additional stimulation location in the area on the basal left free wall 20 reduces the standard deviation of the depolarization times of the heart the most. Therefore, in this example the area on the basal left free wall could be selected as a best location for a pacemaker electrode. An updated 3D model of electrical activation of the heart may be generated including intrinsic activation simultaneously with stimulation in the area on the basal left free wall.

The whole procedure may be performed during the implantation procedure to find most optimal pacing sites.

Figure 9:
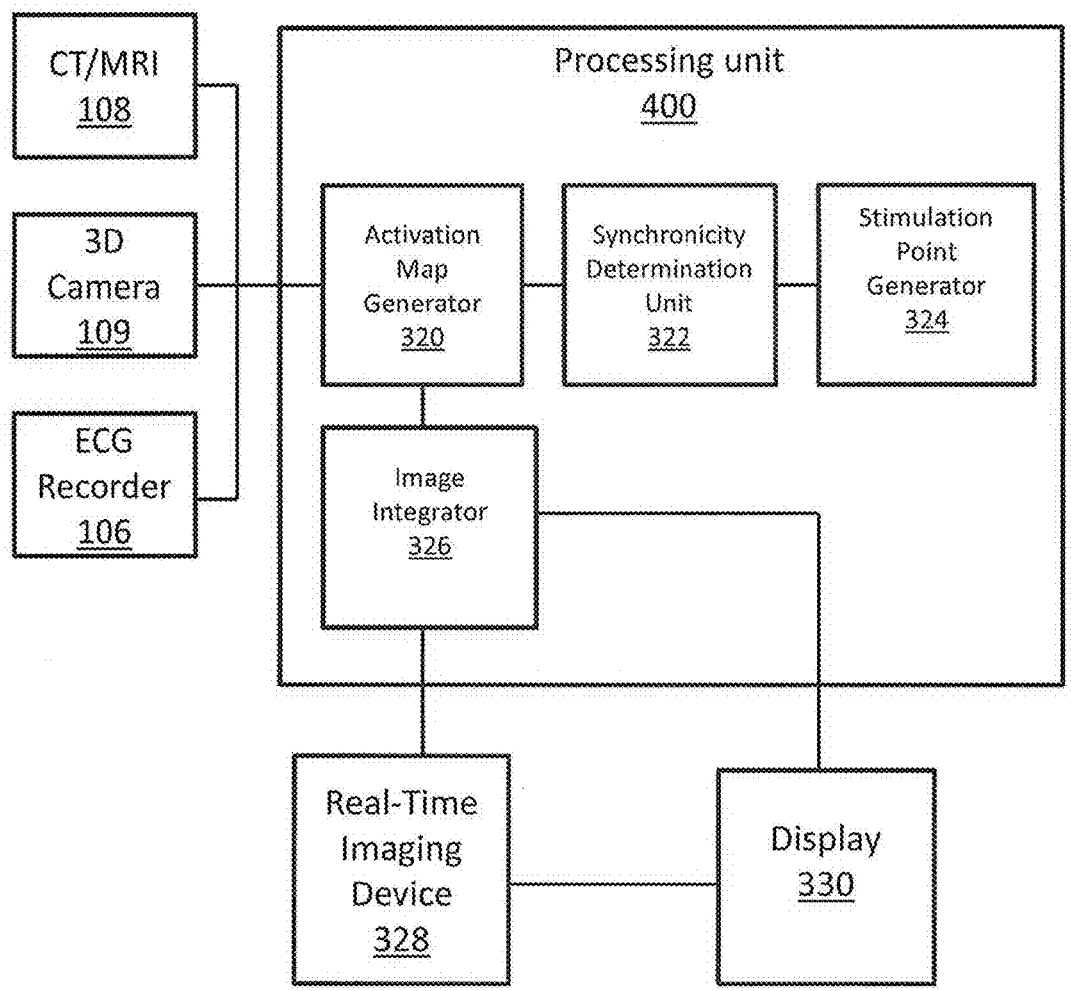
FIG. 9 is a schematic diagram of a surgical imaging system according to various embodiments of the present disclosure.
Figure 10:
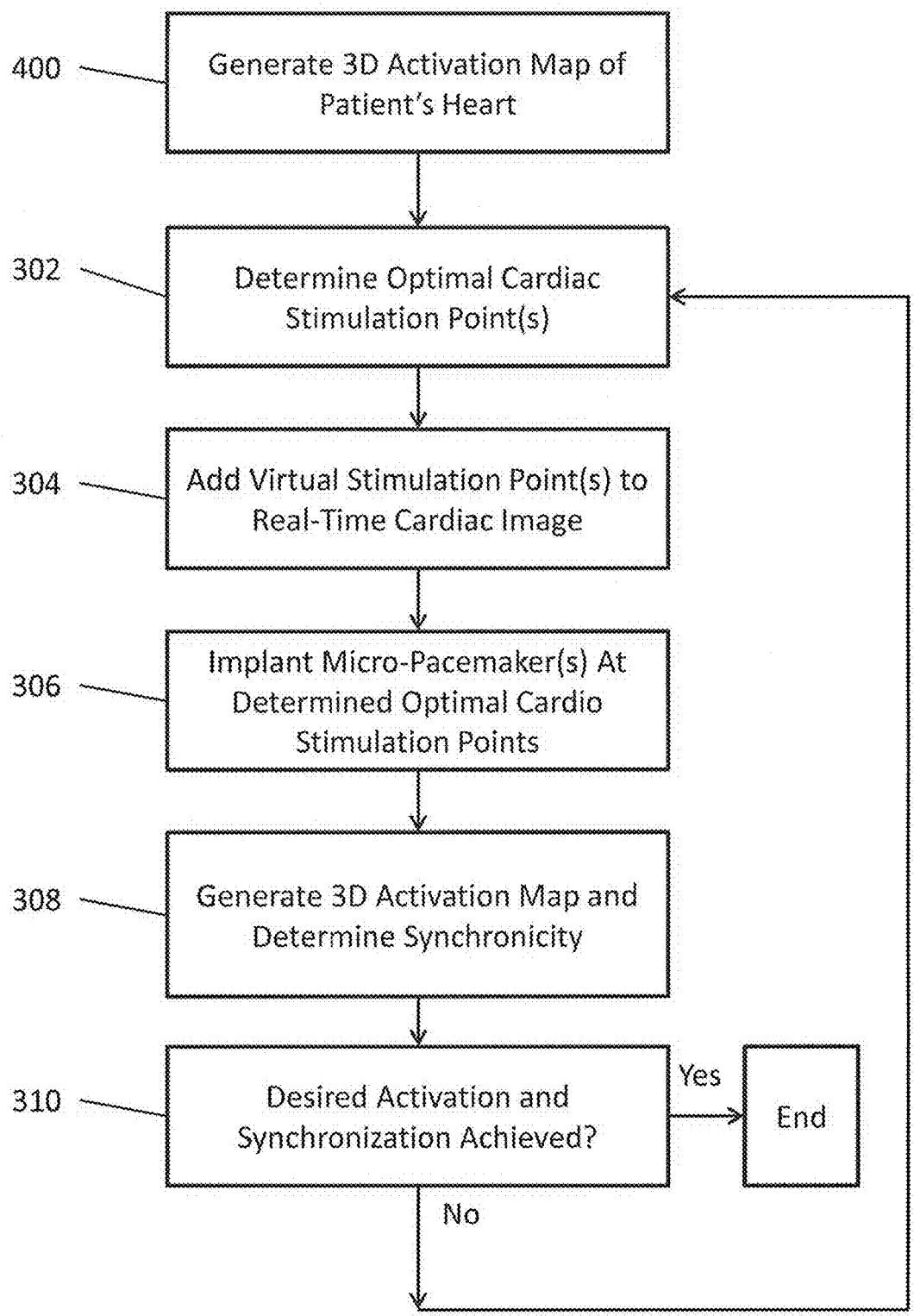
FIG. 10 is a flow diagram of a method of using the system of FIG. 9.

FIG. 9 is a block diagram of a surgical imaging system, according to various embodiments. FIG. 10 is a flow diagram showing a method of implanting a pacemaker using the system of FIG. 9, according to various embodiments. Referring to FIGS. 9 and 10, in step 300, a 3D activation map of the heart of a patient may be generated by a processing unit 400 of the system. In particular, a 3D model of the chest and/or heart of the patient may be generated by a CT or MRI device 108, ECG data of the patient may be recorded by an ECG recorder 106, and a 3D image of the torso of the patient may be generated by a 3D camera 109.

This data may be provided to an activation map generator 320 of the processing unit 400. The ECG data may include extrinsic and/or intrinsic stimulation signals received from the patient.

In step 302, one or more optimal cardiac stimulation points may be determined and added to the activation map. For example, the activation map may be provided to a synchronicity determining unit to determine cardiac synchronicity. This data may then be used by a virtual stimulation point generator 324 to identify stimulation points corresponding to maximized predicted amounts of heart activation and/or synchronization. The stimulation points may be based on a difference between LV and RV activation times, earliest and/or latest activation of the LV and/or RV, a detected depolarization wave blockage, or the like, for example. The stimulation points may be displayed on the activation map.

In step 304, stimulation points may be added to the activation map as virtual stimulation points. For example, the activation map and images generated by a real-time imaging device 328, such as a fluoroscope, a radiography device, an X-ray computed tomography (CT) device, or the like, may be provided to an image integrator 326. The image integrator 326 may compare and/or align the activation map and the real-time images. Based on the comparison and/or alignment, the activation point(s) may be added to the real-time images as virtual activation point(s), to produce modified real-time images. The modified real-time images may be provided to a display 330.

The modified real-time images may show the location of a pacing device. Herein the term "pacing device" may refer to one or more micro-pacemakers or pacemaker electrodes. A physician may use the modified real-time images shown in the display 330 to align a pacing device with the virtual activation point.

In step 306, a pacing device may be implanted into the patient at the virtual activation point. For example, a micro pace-maker may be implanted directly at each virtual activation point.

In step 308, the pacing device may be activated to electrically stimulate the heart. Another (e.g., updated) 3D activation map may be generated to show the effect of the stimulation. The activation map may be used to detect heart activation and/or synchronicity.

In step 310, a determination may be made whether the detected heart activation and/or synchronicity is sufficient restore a desired amount of heart function. If so, the pacemaker(s) may be sutured in place and the procedure may end. If not, new cardiac stimulation point(s) may be generated in step 302, based on the data generated in step 308. For example, one or more virtual stimulations points may be moved to new locations, and/or additional virtual stimulation points may be added. The virtual stimulation points may then be added to the real-time cardiac image in step 304.

In other embodiments, other pacing parameters may be adjusted based on the activation map. For example, the pacing interval at which the LV and RV are stimulated may be adjusted to achieve a desired activation and/or synchronization.

In other embodiments, multi-electrode leads may be implanted, with each electrode being disposed at a different location. The activation map may be used to select which electrodes are used during stimulation of the heart. For example, in some embodiments four-electrode leads may be implanted, and the synchronization map may be used to select a particular electrode, or combination of electrodes, for cardiac stimulation based on a desired activation and/or synchronization.

In some embodiments, the activation map may be used to determine whether CRT is appropriate for a patient. For example, if the cardiac output of a patient is not predicted to achieve an acceptable level after optimally placing pacemaker(s) or pacing leads, it may be determined that CRT is not appropriate for the patient.

In various embodiments, a workstation that may be use that includes the processing unit 400, the display 330, and wired or wireless connections to other hardware such as the CT/MRI device 108, the 3D camera 109, the ECG recorder 106, and/or the real-time imaging device 328. The workstation may also include an interface for controlling a surgical device, such as a catheter implantation device or other robotic surgical device.

Over time, a patient's response to CRT may change, for example, due to changes in a patient's response to pacing stimulation. Accordingly, various embodiments include a post-implantation procedure for optimizing stimulation parameters, such as, stimulation delay timing and/or stimulation electrode selection. The procedure may occur a number of months after the implantation procedure.

Figure 11:
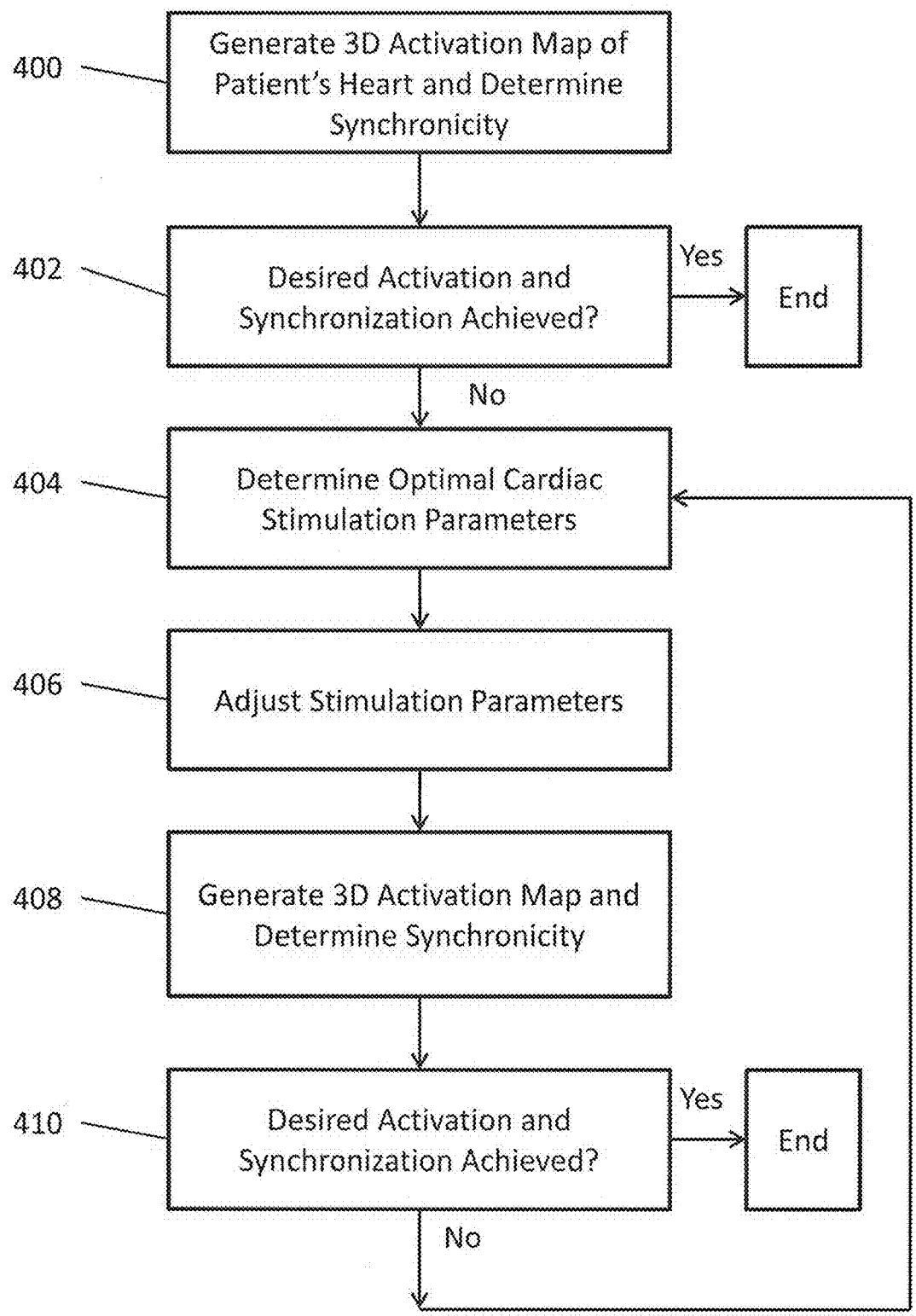
FIG. 11 is a process flow diagram of a post-implantation method using the system of FIG. 9.

FIG. 11 is a flow diagram showing a post-implantation method of optimizing CRT using the system of FIG. 9 according to various embodiments. Referring to FIGS. 9 and 11, in step 400, a 3D activation map of the heart of a patient may be generated by a processing unit 400 of the system. In particular, a 3D model of the chest and/or heart of the patient may be generated by a CT or MRI device 108. Additionally, ECG data of the patient may be recorded by an ECG recorder 106, and a 3D image of the torso of the patient may be generated by a 3D camera 109. This data and the 3D model may be provided to an activation map generator 320 of the processing unit 400. The ECG data may include extrinsic and/or intrinsic stimulation signals received from the patient.

In step 402, a determination may be made whether the detected heart activation and/or synchronicity is sufficient to restore a desired amount of heart function. If so, the stimulation parameters may be unchanged and the procedure may end. If not, the method may proceed to step 404.

In step 404, optimal stimulation parameters may be selected based on the activation map. For example, the delay between the stimulation of the right and left ventricles may be increased or decreased.

In some embodiments, such as when a patient has multi-electrode leads implanted, one or more of the electrodes may be active during stimulation, while the remaining electrode(s) may be inactive. As such, step 404 may include determining whether a different combination of active and inactive electrodes provides optimal cardiac stimulation based on a desired activation and/or synchronization.

In step 406, one or more of the above stimulation parameters may be adjusted based on the determination made in step 404. In step 406, an activation map may be generated based on the adjusted stimulation parameters.

In step 410, if a desired activation and/or synchronization is generated, the method may end. If not, the method may return to step 404.

The preceding description of the disclosed embodiments is provided to enable any person skilled in the art to make or use the present invention. Various modifications to these embodiments will be readily apparent to those skilled in the art, and the generic principles defined herein may be applied to other embodiments without departing from the scope of the claims. Thus, the present invention is not intended to be limited to the aspects and/or embodiments shown herein but is to be accorded the widest scope consistent with the following claims and the principles and novel features disclosed herein.

What is claimed is:

1. A cardiac resynchronization method, comprising:
generating and displaying on a display unit a three-dimensional (3D) activation map showing the propagation of electrical signals through a heart of a patient;
identifying a stimulation point on the heart for cardiac resynchronization;
displaying a real-time image of the heart on the display unit;
aligning the display of the real-time image with the display of the 3D activation map on the display unit;
identifying a first location on the real-time image that corresponds to the stimulation point;
displaying a virtual activation point on the real-time image at the first location;
displaying on the real-time image a pacing device as the pacing device is implanted into the patient;
aligning the pacing device with the virtual stimulation point so that the pacing device is located at the identified stimulation point; and
stimulating the heart at the stimulation point using the pacing device,
wherein the real-time image comprises one or more images of the heart received from a fluoroscope, a radiography device, or an X-ray computed tomography (CT) device.

2. The method of claim 1, further comprising:
updating the activation map based on the stimulation provided by the pacing device; and
determining whether the heart has at least a predetermined level of synchronization, based on the updated activation map.

3. The method of claim 2, wherein when the heart is determined not have a predetermined level of synchronization, the method further comprises:
identifying a second stimulation point on the heart for cardiac resynchronization;
identifying a second location on the real-time image that corresponds to the stimulation point;
adding a second virtual activation point at the second location to the real-time image displayed on the display unit; and
moving the pacing device to the second stimulation point.

4. The method of claim 2, wherein when the heart does not have a predetermined level of synchronization, the method further comprises:
identifying a second stimulation point on the heart for cardiac resynchronization;
identifying a second location on the real-time image that corresponds to the stimulation point;
adding a second virtual activation point at the second location to the real-time image displayed on the display unit; and
adding a second pacing device to the second stimulation point.

5. The method of claim 1, wherein the stimulation point comprises a point in a left ventricle of the heart where a depolarization wave is delayed or begins.

6. The method of claim 1, wherein the pacing device is a micro-pacemaker or pacemaker electrode leads.

7. The method of claim 1, wherein:
identifying a stimulation point on the heart for cardiac resynchronization further comprises identifying multiple stimulation points on the heart; and
displaying a virtual activation point on the real-time image comprises displaying a virtual stimulation point for each identified stimulation point.

8. The method of claim 7, wherein implanting a pacing device into the patient at the identified stimulation point comprises implanting a micro-pacemaker at each virtual stimulation point.

9. The method of claim 1, wherein the real-time image comprises sequential X-ray images.

10. A cardiac resynchronization system, comprising:
a processing unit comprising:
an activation map generator configured to generate a three-dimensional (3D) activation map of the heart of a patient;
a synchronicity determination unit configured to calculate ventricle synchronicity of the heart, based on the activation map;
a stimulation point generator configured to a identify stimulation point on the heart for increasing the synchronicity of the heart; and
an image integrator configured to align the real-time images of the heart with the 3D activation map and add virtual stimulation points to the real-time images, the virtual stimulation points corresponding to the identified stimulation points; and
a display coupled to the processing unit and configured to display the real-time images of the heart and images generated by the image integrator,
wherein the real-time images comprise images of the heart received from a fluoroscope, a radiography device, or an X-ray computed tomography (CT) device.

11. The imaging system of claim 10, wherein the activation map generator is configured to generate the 3D activation map based on electrocardiograph (ECG) data of the patient, three-dimensional (3D) image data of the thorax of the patient, and a 3D anatomical model of the patient.

12. The imaging system of claim 10, wherein the image generator is configured to add the virtual stimulation points to the real-time images.

13. The imaging system of claim 10, wherein the activation map generator is configured to update the activation map based on ECG data received after a pacing device has been implanted in the patient and activated.

14. The imaging system of claim 13, wherein the synchronicity determination unit is configured to recalculate the ventricle synchronicity, after the pacing device has been implanted and activated.

15. The imaging system of claim 13, wherein the stimulation point generator is configured to determine whether the stimulation point should be moved, based on the recalculated ventricle synchronicity.

16. The imaging system of claim 13, wherein the stimulation point generator is configured to determine whether a second stimulation point should be added, based on the recalculated ventricle synchronicity.

17. The imaging system of claim 13, wherein the pacing device comprises a micro-pacemaker or pacemaker electrode leads.

18. The imaging system of claim 10, wherein the display is configured to simultaneously display the activation map and the real-time images.

19. The imaging system of claim 10, wherein the stimulation point generator is configured to identify multiple stimulation points on the heart.

* * * * *